(12) United States Patent
Ingber et al.

(10) Patent No.: US 9,962,698 B2
(45) Date of Patent: May 8, 2018

(54) REMOVING BUBBLES IN MICROFLUIDIC SYSTEMS

(71) Applicant: PRESIDENT AND FELLOWS OF HARVARD COLLEGE, Cambridge, MA (US)

(72) Inventors: Donald E. Ingber, Boston, MA (US); Geraldine A. Hamilton, Cambridge, MA (US); Daniel Levner, Boston, MA (US); Christopher Hinojosa, Cambridge, MA (US); Daniel Patterson, Somerville, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 42 days.

(21) Appl. No.: 14/424,195

(22) PCT Filed: Sep. 4, 2013

(86) PCT No.: PCT/US2013/057992
§ 371 (c)(1),
(2) Date: Feb. 26, 2015

(87) PCT Pub. No.: WO2014/039514
PCT Pub. Date: Mar. 13, 2014

(65) Prior Publication Data
US 2015/0209783 A1 Jul. 30, 2015

Related U.S. Application Data

(60) Provisional application No. 61/696,997, filed on Sep. 5, 2012, provisional application No. 61/735,215, filed on Dec. 10, 2012.

(51) Int. Cl.
*B01D 19/00* (2006.01)
*B01L 3/00* (2006.01)
(Continued)

(52) U.S. Cl.
CPC ...... *B01L 3/502723* (2013.01); *B01D 17/085* (2013.01); *B01D 19/0031* (2013.01);
(Continued)

(58) Field of Classification Search
CPC .......... B01D 19/0031; B01D 2053/222; B01D 63/088; B01L 3/502715; B01L 3/502723;
(Continued)

(56) References Cited

U.S. PATENT DOCUMENTS

| 2003/0064507 A1 | 4/2003 | Gallagher et al. |
| 2003/0150792 A1* | 8/2003 | Koehler ............... B01D 63/088 210/321.84 |
| 2004/0092033 A1* | 5/2004 | Gustafson .......... B01D 19/0031 436/180 |
| 2005/0167354 A1* | 8/2005 | Caze ...................... B01D 61/18 210/321.84 |
| 2006/0090645 A1* | 5/2006 | Kent .................. B01D 19/0031 95/46 |
| 2006/0108287 A1* | 5/2006 | Arnold .................. B01D 63/08 210/638 |
| 2008/0047836 A1* | 2/2008 | Strand ............... B01L 3/502715 204/644 |
| 2009/0045532 A1* | 2/2009 | Young ................ B01D 19/0031 264/1.1 |

(Continued)

FOREIGN PATENT DOCUMENTS

| WO | WO 2010/009307 A2 * | 1/2010 | .............. C12M 3/06 |
| WO | 20121064172 A1 | 5/2012 | |

*Primary Examiner* — Jason M Greene
(74) *Attorney, Agent, or Firm* — Nixon Peabody LLP

(57) ABSTRACT

A microfluidic system includes a microfluidic device connected to a bubble trap device whereby fluid flowing to the microfluidic device passes through the bubble trap device to remove gas bubbles prior to entering the microfluidic device. The bubble trap can include a separation chamber and an exhaust chamber separated by a hydrophobic porous membrane and gas bubbles in the fluid entering the separation chamber pass through the hydrophobic porous membrane into the exhaust chamber while the fluid remains in the separation chamber. The bubble trap can be formed by bonding a first body portion to a first side of the hydrophobic porous membrane and bonding a second body portion to a second side of the hydrophobic porous membrane. The exhaust chamber can be connected to an elongated exhaust channel that limits the evaporation losses of the fluid through the hydrophobic porous membrane.

25 Claims, 13 Drawing Sheets

(51) Int. Cl.
 *C12M 1/107* (2006.01)
 *C12M 1/04* (2006.01)
 *C12M 3/06* (2006.01)
 *B01D 63/08* (2006.01)
 *B01D 71/36* (2006.01)
 *B01D 17/00* (2006.01)

(52) U.S. Cl.
 CPC ........... *B01D 63/088* (2013.01); *B01D 71/36* (2013.01); *B01L 3/502715* (2013.01); *C12M 23/16* (2013.01); *C12M 23/24* (2013.01); *C12M 23/36* (2013.01); *B01D 2325/38* (2013.01); *B01L 2200/0684* (2013.01); *B01L 2300/06* (2013.01); *B01L 2300/087* (2013.01); *B01L 2300/0816* (2013.01); *B01L 2300/0864* (2013.01); *B01L 2300/0874* (2013.01); *B01L 2300/0877* (2013.01); *B01L 2300/0887* (2013.01)

(58) Field of Classification Search
 CPC ......... B01L 2200/0684; B01L 2300/06; B01L 2300/0864; B01L 2300/087; B01L 2300/0874; B01L 2300/0877; B01L 2300/0887; C12M 23/16; C12M 23/24; C12M 23/36

See application file for complete search history.

(56) References Cited

U.S. PATENT DOCUMENTS

| | | | |
|---|---|---|---|
| 2009/0211977 A1* | 8/2009 | Miller | B01D 63/088 210/646 |
| 2010/0003765 A1* | 1/2010 | Dixon | B01D 19/0073 436/172 |
| 2010/0012586 A1 | 1/2010 | Angelescu et al. | |
| 2011/0151479 A1* | 6/2011 | Stevens | G01N 33/54366 435/7.1 |
| 2011/0155667 A1* | 6/2011 | Charest | B01D 63/088 210/651 |
| 2011/0250585 A1 | 10/2011 | Ingber et al. | |
| 2012/0160096 A1* | 6/2012 | Gottlieb | B01D 19/0031 95/46 |
| 2012/0245042 A1* | 9/2012 | Liu | B01D 19/0031 506/7 |
| 2012/0309082 A1* | 12/2012 | Jung | B01L 3/502723 435/289.1 |

* cited by examiner

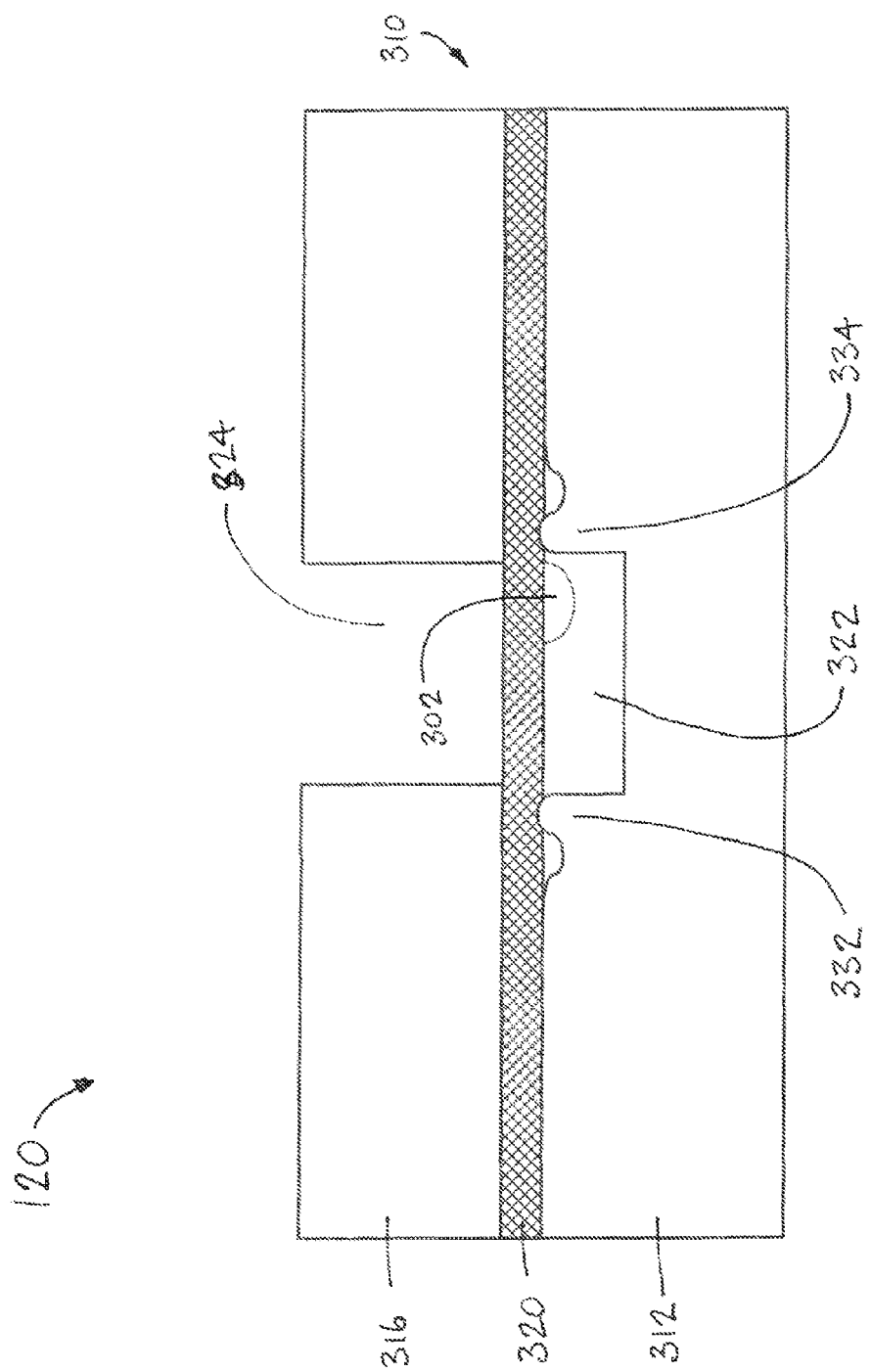

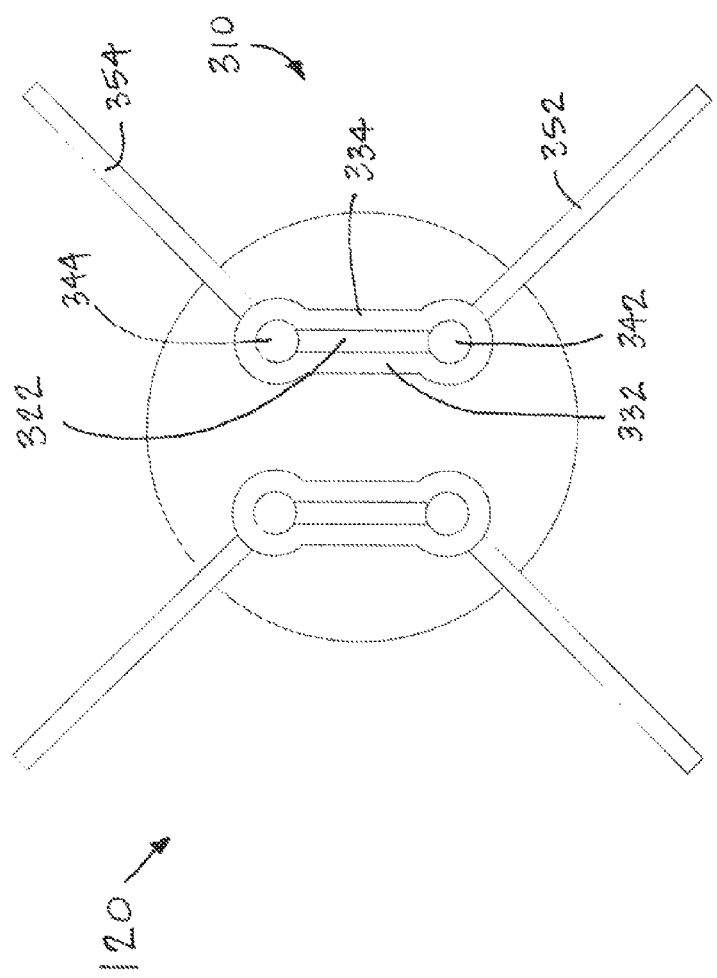

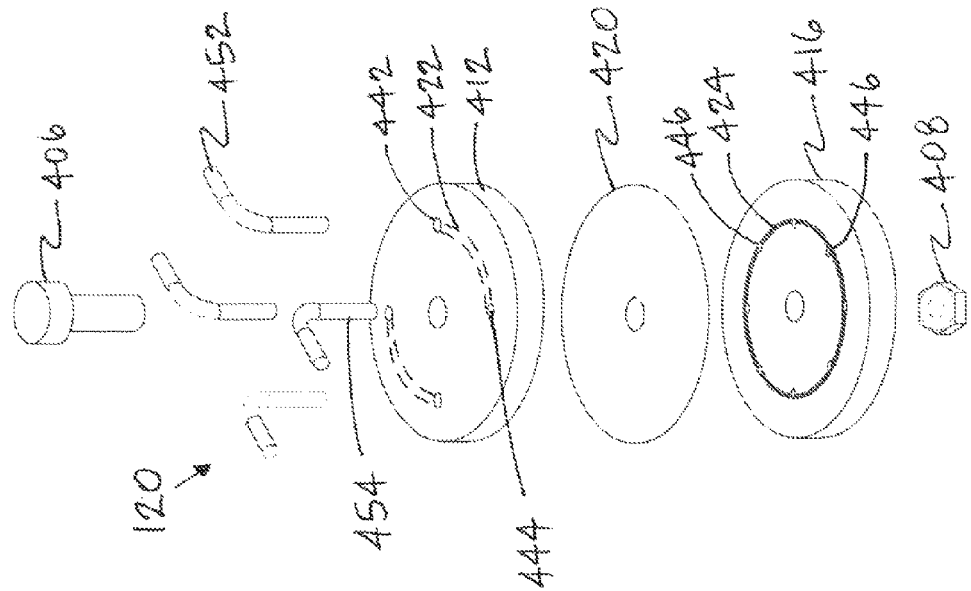
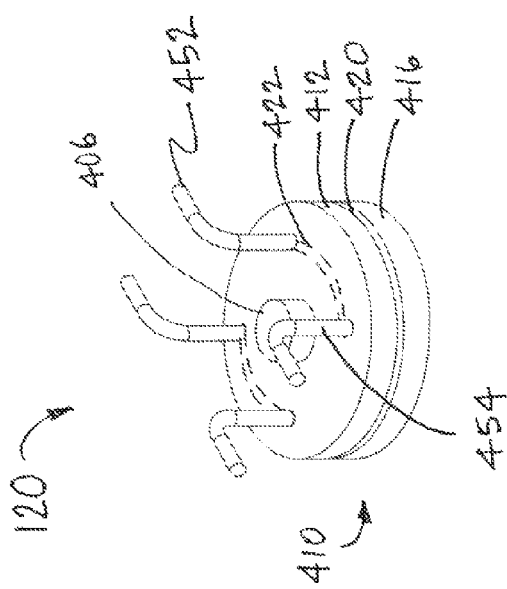
Fig. 4B
Fig. 4A

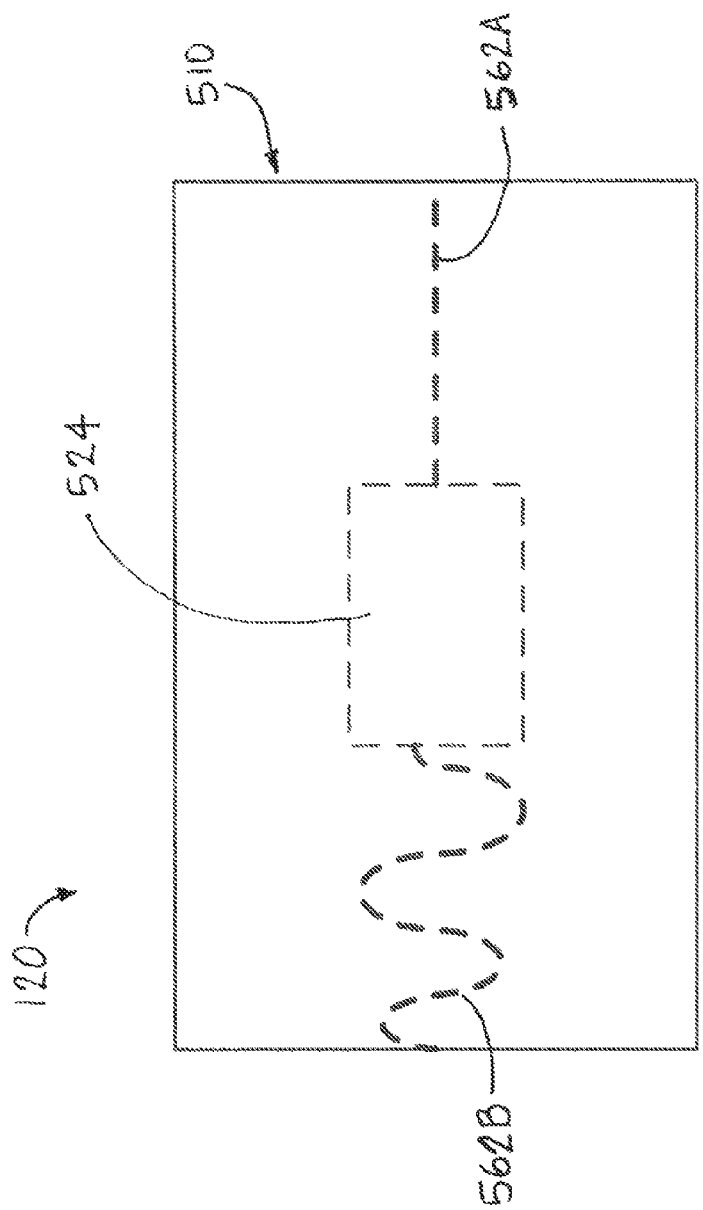

REMOVING BUBBLES IN MICROFLUIDIC SYSTEMS

CROSS-REFERENCE TO RELATED APPLICATIONS

This application is a 35 U.S.C. § 371 National Phase Entry Application of International Patent Application No. PCT/US2013/057992, filed Sep. 4, 2013, which designates the U.S., and claims benefit under 35 U.S.C. § 119(e) of U.S. Provisional Application No. 61/696,997 filed on Sep. 5, 2012 and U.S. Provisional Application No. 61/735,215 filed on Dec. 10, 2012, the contents of each of which are incorporated herein by reference in their entireties.

GOVERNMENT SUPPORT

This invention was made with government support under grant no. W911NF-12-2-0036 awarded by DARPA/U.S. Department of Defense. The government has certain rights in the invention.

REFERENCE TO MICROFICHE APPENDIX

Not Applicable

BACKGROUND

Technical Field of the Invention

The present invention is directed to microfluidic systems and devices for use in microfluidic systems that can be used to remove bubbles. More specifically, the present invention is directed to bubble separating or trapping devices that can be used to remove bubbles from fluids flowing into microfluidic devices, such as, organ-on-a-chip or organ chip devices.

Description of the Prior Art

In the prior art, fluidic and microfluidic devices are typically interconnected into systems that include many individual fluidic and microfluidic components connected by a complicated and cumbersome arrangement of tubing, valves and pumps. The fluidic and microfluidic components can include one or more reservoirs, pumps, valves, mixers, sensors, analytical devices, collection devices, and organ-on-a-chip devices. When the components are connected and disconnected as well as during normal operation, gas bubbles can be introduced or formed in the fluids that flow through these fluidic and microfluidic devices and systems. In some configurations, these gas bubbles, such as air bubbles, can negatively impact the operation of the system and can harm the biologic elements that can reside in the various components of the system.

SUMMARY

The present invention is directed to fluidic and microfluidic devices and systems that can be used to grow and sustain biologic elements such as cells, tissues and organs. In operation, these fluidic and microfluidic devices and systems utilize the flowing fluids to distribute media, nutrients, and other materials useful for culturing and sustaining the biologic cells, tissues and organs. The introduction of air or gas bubbles into these systems can impede the flow of fluid through the system and potentially harm the cells, tissues and organs. In addition, bubbles inadvertently introduced into the system can significantly and negatively affect device operation and experimental outcomes. In accordance with some embodiments of the invention, a bubble trap can be integrated into or directly connected to fluidic and microfluidic devices to avoid the problems caused by bubbles inadvertently introduced in to the system.

In accordance with some embodiments of the invention, the microfluidic system includes a microfluidic device having a body and a central channel, the central channel having an inlet for introducing fluid to the central channel and a bubble trap having a separation chamber and an exhaust chamber separated by a hydrophobic porous membrane. The separation chamber can be connected to a fluid channel and the fluid channel can be connected to the inlet of the microfluidic device so that fluid from the separation chamber can flow into the central channel of the microfluidic device. In operation, fluid and gas bubbles enter the separation chamber and the fluid from the separation chamber flows through the fluid channel to the inlet of the microfluidic device while gas bubbles pass through the hydrophobic porous membrane into the exhaust chamber. In order to reduce evaporation losses of the fluid through the hydrophobic porous membrane, the exhaust channel can be connect to the ambient environment by an elongated exhaust channel that increases the diffusion distance from the hydrophobic porous membrane to the ambient environment.

The bubble trap can be constructed by bonding a first body portion to a first side of the hydrophobic porous membrane and bonding a second body portion to a second side of the hydrophobic porous membrane. The separation chamber can be formed in the first body portion and the exhaust chamber can be formed in the second body portion. In accordance with some embodiments of the invention, the first body portion can be formed by bonding a separation chamber defining layer to a base layer. In accordance with some embodiments of the invention, the second body portion can be formed by bonding an exhaust chamber defining layer to a top layer.

In accordance with implementations of the invention, one or more of the following capabilities may be provided. The bubble trap can be fabricated by bonding a plurality of layers together into a single structure. The bubble trap can fabricated by removably attaching a plurality of layers together, such as by the use of threaded fasteners or clamps that enable the hydrophobic porous membrane to be removed and replaced as well as to enable the separation chamber and/or the exhaust chamber to be cleaned. The bubble trap can be adapted and configured to separate bubbles that do not rise to the top of the separation chamber. The bubble trap can include an elongate exhaust channel and the length of the exhaust channel can be selected to limit evaporation losses through the hydrophobic porous membrane.

These and other capabilities of the invention, along with the invention itself, will be more fully understood after a review of the following figures, detailed description, and claims.

BRIEF DESCRIPTION OF THE FIGURES

The accompanying drawing figures, which are incorporated into this specification, illustrate one or more exemplary embodiments of the inventions and, together with the detailed description, serve to explain and illustrate the principles and applications of these inventions. The drawings and detailed description are illustrative, and not limiting, and can be adapted and modified without departing from the scope and spirit of the inventions.

FIGS. 3A and 3B show diagrammatic views of a bubble trap device formed by a gasketing embossment according to some embodiments of the invention.

FIG. 4A shows a diagrammatic view of a standalone bubble trap device according to some embodiments of the invention.

FIG. 4B shows an exploded diagrammatic view of the standalone bubble trap device shown in FIG. 4A.

FIG. 5 shows a diagrammatic view of a bubble trap device having elongated exhaust channels to control evaporation according to some embodiments of the invention.

DETAILED DESCRIPTION OF PREFERRED EMBODIMENTS

Figure 1:
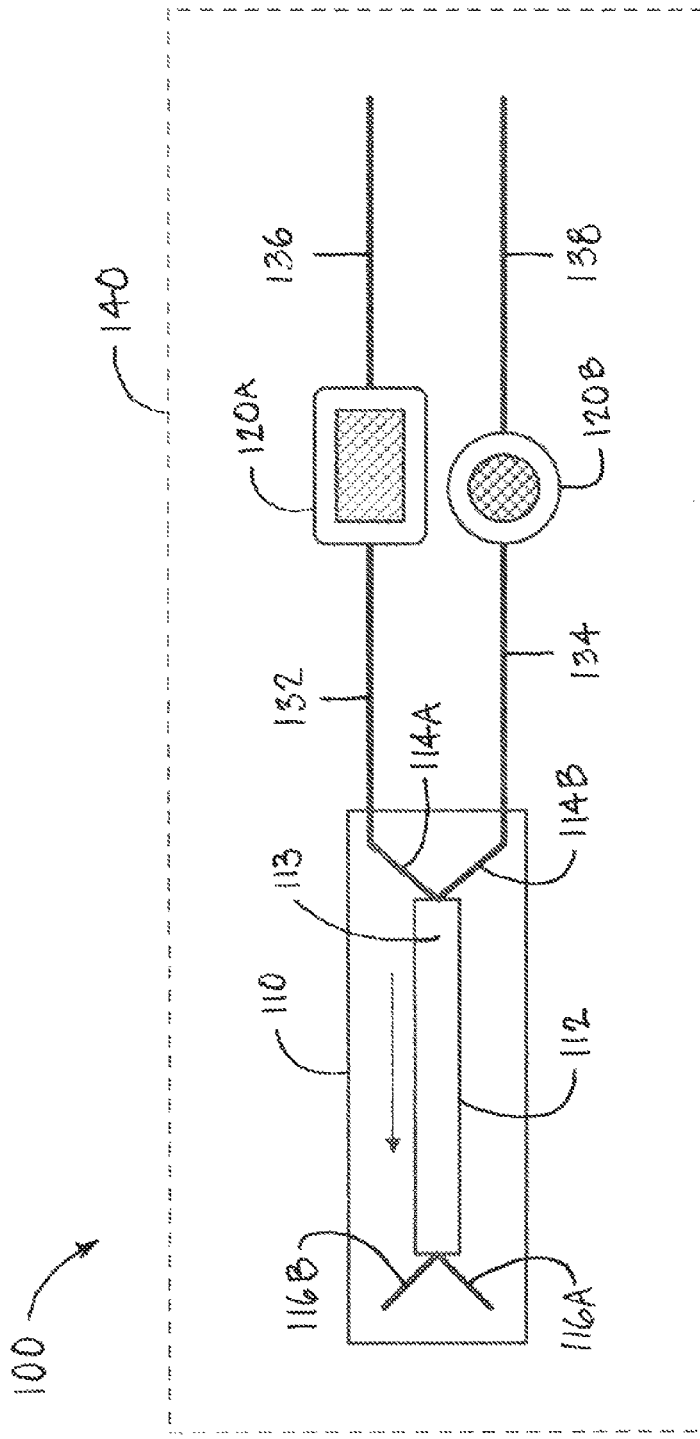
FIG. 1 shows a diagrammatic view of a microfluidic system according to the invention.

For purposes of illustration, aspects of the present invention will be described in the context of diagrammatic examples of microfluidic systems according to embodiments of the invention. As used herein the terms fluidic and microfluidic, unless the context clearly indicated otherwise, are used interchangeably. While the inventions may, in some circumstances, be better suited for use with microfluidic devices and systems, the inventions may, in some circumstances, also be better suited for use with fluidic devices and system.

The invention is directed to a microfluidic system that includes one or more microfluidic devices connected to other devices or components that make up a microfluidic system or a part thereof. As used herein the term microfluidic device is intended to refer to devices that include one or more microfluidic channels that are adapted to carry fluids between components. In accordance with some embodiments of the invention, the cross-sectional distance of the channels of a microfluidic device will be in the range from 1.0 micron to 10,000 microns. In accordance with some embodiments, the cross-sectional distance of the channel in a microfluidic device will be in the range from 100 microns to 1000 microns, or more.

In accordance with some embodiments of the invention, one or more of the microfluidic channels of the microfluidic device can be adapted to host biologic components such as cells, tissues and organs. One or more microfluidic channels can be seeded with cells that can cultured and develop into functioning cell colonies, tissues and organs (or portions thereof). In accordance with some embodiments of the invention, one or more of the microfluidic channels can include a membrane that separates the microfluidic channel into an upper microfluidic channel and a lower microfluidic channel and cells can be cultured on the membrane to form functioning cell colonies, tissue and organ portions. Media can be delivered through one or both channels to culture and sustain the cells, tissues and organs. These microfluidic devices are also referred to as organ-on-a-chip or organ-chip devices. Examples of organ-on-a-chip or organ-chip devices that can be used in the methods and systems according to the invention include, for example, in U.S. Provisional Application No. 61/470,987, filed Apr. 1, 2011 and corresponding PCT Application No. PCT/US12/31864, filed Apr. 2, 2012; U.S. Provisional Application No. 61/492,609, filed Jun. 2, 2011 and corresponding PCT Application No. PCT/US12/40188, filed May 31, 2012; U.S. Provisional Application No. 61/447,540, filed Apr. 20, 2011 and corresponding U.S. patent application Ser. No. 13/452,687, filed Apr. 20, 2012; U.S. Provisional Application No. 61/449,925, filed Mar. 7, 2011; and U.S. Provisional Application No. 61/569,029, filed on Dec. 9, 2011 and corresponding PCT Application No. PCT/US12/68766, filed Dec. 10, 2012; U.S. patent application Ser. No. 13/054,095, filed Jun. 30, 2011, and corresponding PCT Application No. PCT/US09/50830, filed Jul. 16, 2009; and PCT Application No. PCT/US2010/021195, filed Jan. 15, 2010, the contents of each application is incorporated herein by reference in its entirety. Muscle organ-chips are described, for example, in U.S. Provisional Patent Application Ser. No. 61/569,028, filed on Dec. 9, 2011, U.S. Provisional Patent Application Ser. No. 61/697,121, filed on Sep. 5, 2012, and corresponding PCT Application No. PCT/US12/68787, filed on Dec. 10, 2012, the contents of each application is incorporated herein by reference in its entirety. The organ-chips can also include control ports for application of mechanical modulation (e.g., side chambers to apply cyclic vacuum, as in the Lung Chip described in the PCT Application No.: PCT/US2009/050830) and electrical connections (e.g., for electrophysiological analysis of muscle and nerve conduction). A similar approach of producing the Lung Chips with or without aerosol delivery capabilities (which can be extended to produce other organ-chips, e.g., heart chips and liver chips) is described, e.g., in the PCT Application No.: PCT/US09/50830 and U.S. Provisional Application Nos. 61/483,837, filed on May 9, 2011 and 61/541,876, filed on Sep. 30, 2011, and corresponding PCT Application No. PCT/US12/37096, filed on May 9, 2012, the contents of each application is incorporated herein by reference in its entirety. Examples of cartridges are described in, for example, PCT Application No. PCT/US2012/068725, filed Dec. 10, 2012 and U.S. Provisional Application No. 61/696,997, filed on Sep. 5, 2012 and No. 61/735,215, filed on Dec. 10, 2012, contents of each application is incorporated herein by reference in its entirety.

In accordance with some embodiments of the invention, organ-chip devices can be relatively small microfluidic devices making them difficult to handle and because of their small size, difficult to incorporate into microfluidic systems. In accordance with some embodiments of the invention, a series of steps can be used to produce the functioning cells, tissues and organs in the organ-chip devices so that the device can be subsequently used to study the effects of stimuli, agents, drugs, and other therapeutic treatment of the cells, tissues and organs. Thus, the organ-chip device can be connected to one system for culturing the cells and another system which maintains the viability of the cells while they are transported and await use. The organ-chip device can subsequently be connected to one or more additional systems that are used to study the effects of stimuli, agents, drugs, and other therapeutic treatment on the cells, tissues and organs. These steps can involve connecting and disconnecting the microfluidic device from other components in various configurations and can result in air or gas bubbles forming in the channels that facilitate interconnection. Air or gas bubbles can also form as a result of changes in environmental pressure or as a result of a chemical reaction. These air or gas bubbles can harm the cells, tissues, and organs as they develop and are maintained within the microfluidic device. The air or gas bubbles can impact fluid flow and affect the validity of the experiments on the cells, tissues, and organs. Therefore, it is desirable to remove the bubbles from the fluids that flow into these microfluidic devices.

In accordance with some embodiments of the invention, a bubble trap device or component can be used to remove air or gas bubbles from the fluid before it enters the microfluidic device. In accordance with some embodiments of the invention, the bubble trap can include a hydrophobic, porous membrane that allows air or gas bubbles to pass through the membrane while preventing or limiting the flow of the fluid through the membrane. In accordance with some embodiments of the invention, the bubble trap can also be adapted to limit evaporation or diffusion of the fluid through the membrane to limit fluid losses of the system.

FIG. 1 shows a diagrammatic view of a microfluidic system 100 according to the invention. The microfluidic system 100 can include a microfluidic device 110 connected to a first bubble trap 120A and a second bubble trap 120B by fluid connections 132 and 134. The fluid connections 132 and 134 can include fluidic and microfluidic tubing as well as microfluidic channels in a cartridge, docking station or housing, generally denoted as 140. The fluid connections 132 and 134 can also include one or more fluid valves that control or direct the flow of fluid through the fluidic connection and/or one or more fluid reservoirs that can be used to store the fluid for a period of time. Examples of microfluidic cartridges are disclosed in U.S. Patent Application No. 61/856,876, filed on Jul. 22, 2013, the contents of which are herein incorporated by reference in its entirety. In these embodiments of the invention, the bubble trap 120A, 120B can be integrated into the cartridge 140, such that all fluid flowing into the microfluidic device 110 has to pass through a bubble trap 102A, 120B. Alternatively, fluidic connections 132 and 134 can be connections created through the use of a microfluidic interconnection system such as that disclosed in U.S. Patent Application No. 61/845,666, filed on Jul. 12, 2013, the contents of which are herein incorporated by reference in its entirety.

The microfluidic device 110 can include a body having one or more microfluidic channels 112 and one or more of the microfluidic channels can include one or more membranes 113, coupled to the body at membrane mounting regions that separate the microfluidic channel into two or more microfluidic channels. In accordance with some embodiments of the invention, the membrane 113 can be rigid or substantially inflexible. In accordance with some embodiments of the invention, the membrane 113 can be flexible or stretchable and a mechanism can be provided to modulate the membrane 113 causing it to flex and stretch. In accordance with some embodiments of the invention, the membrane 113 can be porous and allow molecules and/or cells to pass through. In accordance with some embodiments of the invention, the membrane 113 can be non-porous and prevent the passage of molecules and cells through the membrane. In accordance with some embodiments of the invention, each microchannel can include one or more inlet channels 114A, 114 and one or more outlet channels 116A, 116B that connect each microchannel to a fluid source device or component and a fluid destination device or component. In accordance with some embodiments of the invention, the inlet channels and the outlet channels can terminate at a port that can include a connector that facilitates a fluidic connection with another device or component of the system. In accordance with some embodiments of the invention, the connector can be a Luer Lock™ type connector. In accordance with some embodiments of the invention, the connector can include a hollow needle that pierces a resealable membrane such as that disclosed in U.S. Patent Application No. 61/810,944, filed on Apr. 11, 2013, the contents of which are herein incorporated by reference in its entirety. In accordance with some embodiments of the invention, the connector can include tapered nozzles that fit into tapered holes such as that disclosed in U.S. Patent Application No. 61/839,702, filed on Jun. 26, 2013, the contents of which are herein incorporated by reference in its entirety.

The membrane 113 in the microfluidic device 110 can be treated or coated to support or promote cell attachment or adhesion on one or both sides of the membrane. The membrane 113 of the microfluidic device 110 can be coated with cell adhesion molecules that support or promote the attachment of living cells and promote their organization into living tissues on the upper and/or lower surface of the membrane 113. The cell adhesion coating can include ECM proteins, such as, fibronectin, laminin, vitronectin or tenascin or various collagen types or combinations thereof, and a positively charged molecule to improve cell attachment, that can, for example, be selected from the group consisting of polylysine, chitosan, poly(ethyleneimine) or acrylics polymerized from acrylamide or methacrylamide and incorporating positively-charged groups in the form of primary, secondary or tertiary amines, or quaternary salts. The membrane 113 of the microfluidic device 110 can be porous and the pores can be large enough to only permit exchange of gases and small chemicals, or to permit migration and transchannel passage of large proteins and whole living cells. Examples of cells that can be adhered to one or both sides of the membrane of the microfluidic device include liver, kidney, lung, intestine, bone marrow, immune system, bone, teeth, skin, bacterial and other organ and tissue cells, such as, epithelial and endothelial cells. The cells can be deposited on the membrane and cultured in the microfluidic device. Various stem cells can be cultured on the membrane and, using different culture media, cause the stem cells to differentiate into different cell types.

The bubble trap devices 120A, 120B can be connected to fluidic connections 136, 138 that can carry fluid, possibly containing gas bubbles, into the bubble trap device 120A, 120B, where the gas bubbles can be removed from the fluid before it exits the bubble trap 120A, 120B and flows through fluidic connections 132, 134 to the microfluidic device 110.

Figure 2:
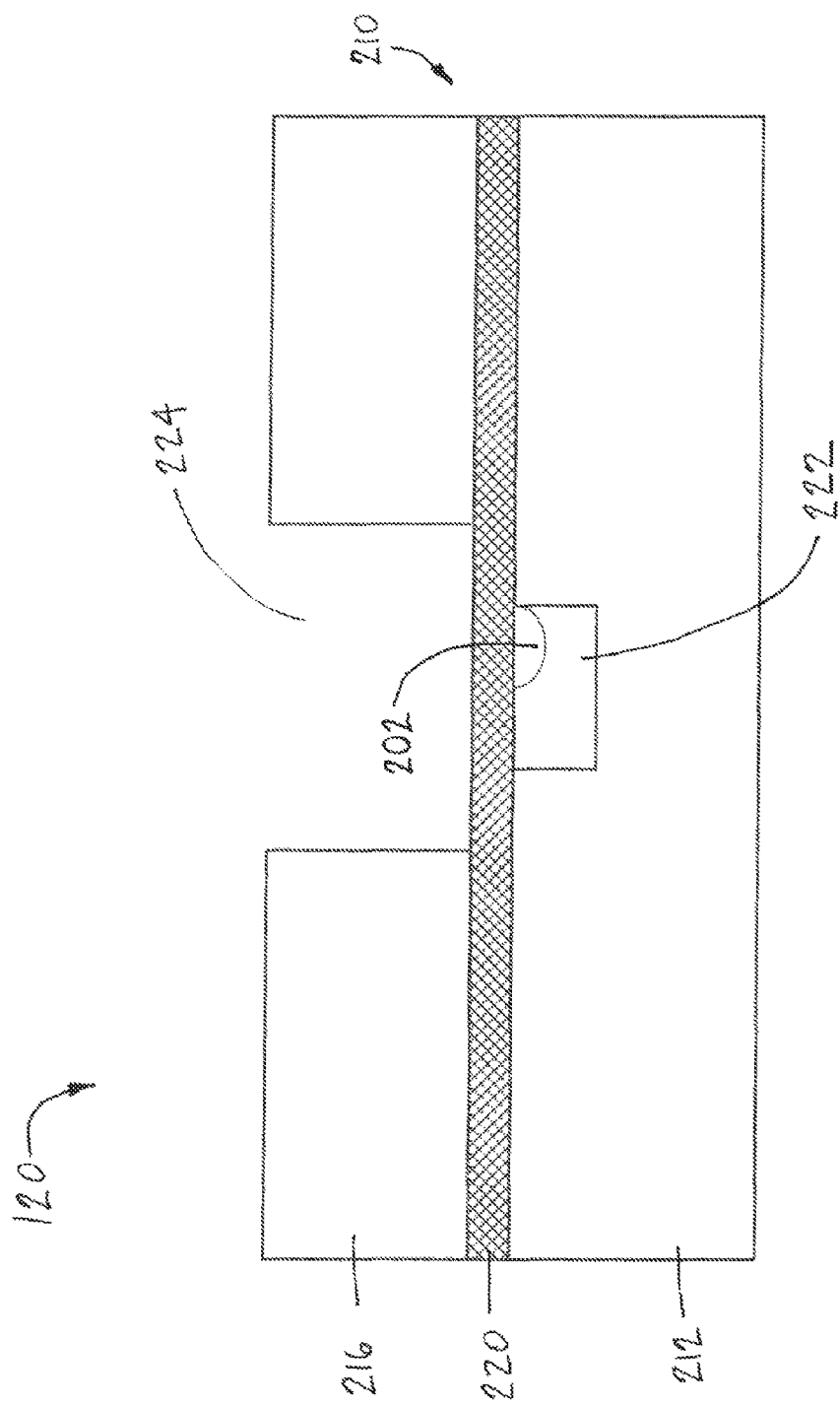
FIG. 2 shows a diagrammatic view of a bubble trap device according to some embodiments of the invention.
Figure 2A:
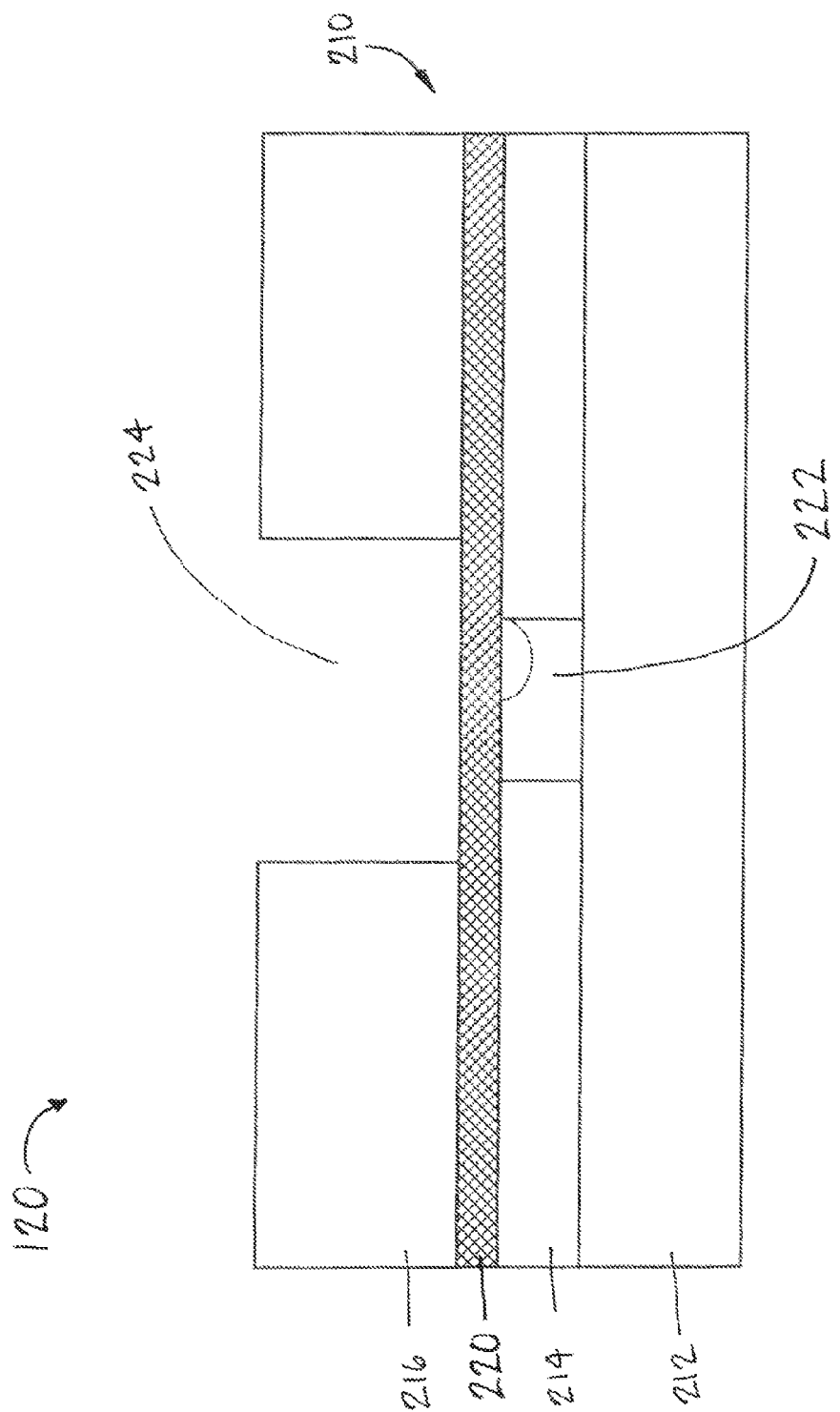
FIG. 2A shows a diagrammatic view of a bubble trap device formed by laminating layers according to some embodiments of the invention.
Figure 2B:
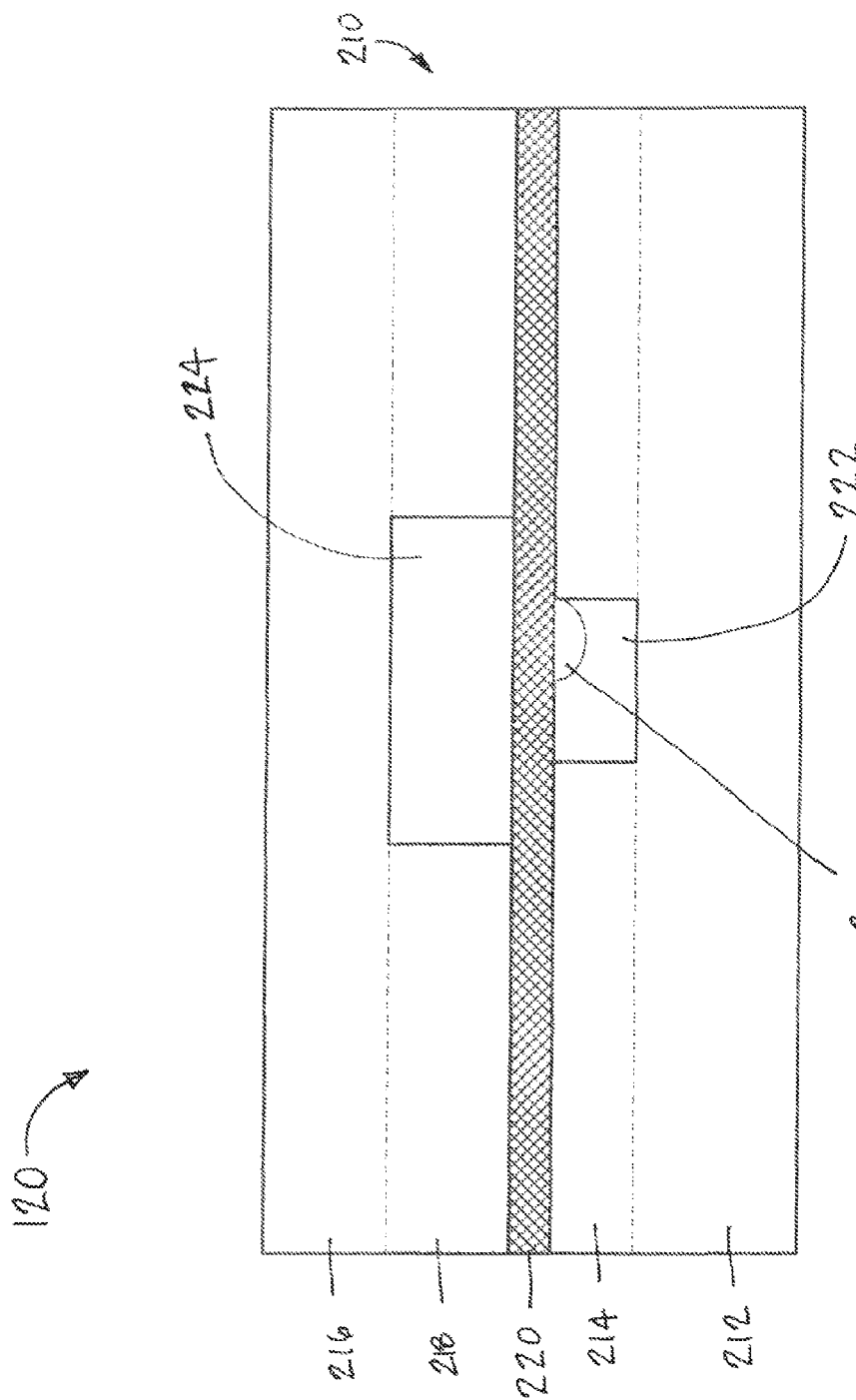
FIG. 2B shows a diagrammatic view of a bubble trap device having a closed exhaust channel according to some embodiments of the invention.

FIGS. 2, 2A and 2B show diagrammatic views of a bubble trap device 120 according to some embodiments of the invention. The bubble trap device 120 can include a body 210 that includes a first body portion 212, a second body portion 216 and a separation membrane 220. The first body portion 212 can include a separation channel or chamber 222 that includes at least a portion of the membrane forming at least a portion of a wall of the separation chamber 222. In operation, fluid containing bubbles 202 can flow into the separation chamber 222 whereby the bubbles 202 pass through a portion of the membrane 220 while the fluid (without bubbles 202) is retained in the chamber 222 and can subsequently flow out of the chamber 222. The bubbles 202 can pass through the membrane 220 into an exhaust chamber 224. In accordance with some embodiments of the invention, as shown in FIGS. 2 and 2A, the exhaust chamber 224 can be open and the gas from the bubbles can be released in to the ambient atmosphere. In accordance with some embodiments of the invention, as shown in FIG. 2B, the exhaust chamber 224 can be a separate chamber or channel that enables the gas from the bubbles to be captured and pumped or drawn in to another device or location for later analysis or further processing. The fluid can include any desirable fluid useful for culturing and/or sustaining the cells, tissue or organ in the microfluidic channel, including, for example, water, saline, water based formulations, blood, blood plasma, other biologic fluids, cell culture media, and mixtures of these materials. The fluid can also include bacteria, viruses, nanoparticles, and toxins.

As shown in FIGS. 2A and 2B, the bubble trap 120 can be constructed by forming individual layers that can be laminated together to form the assembly. The bubble trap body 210 shown in FIG. 2A can be formed by laminating a base layer 212 and a separation chamber defining layer 214 to form a first body portion. The first body portion (composed of the base layer 212 and the chamber defining layer 214) can be laminated to a first side of the membrane 220 and the second body portion 216 can be laminated to a second side of the membrane 220. The bubble trap body 210 shown in FIG. 2B can be formed by laminating a base layer 212 and a separation chamber defining layer 214 to form a first body portion and by laminating a top layer 216 and an exhaust chamber defining layer 218 to form a second body portion. The first body portion (composed of the base layer 212 and the chamber defining layer 214) can be laminated to a first side of the membrane 220 and the second body portion (composed of the top layer 216 and the exhaust chamber defining layer 218) can be laminated to a second side of the membrane 220. In accordance with some embodiments of the invention, the chamber defining layer 214 and/or the exhaust chamber defining layer 218 can include an adhesive layer formed from an adhesive material, for example, an elastomer such as styrene-ethylene/butylene-styrene (SEBS), polyurethane, and silicones such as Polydimethylsiloxane (PDMS) and double-sided adhesive tapes (e.g., 3M double-sided adhesive transfer tape, 3M, St. Paul, Minn.). In accordance with some embodiments of the invention, the base layer 212 and/or the top layer 216 include a rigid material such as acrylic, polystyrene, polypropylene, polycarbonate, glass, epoxy-fiberglass, ceramic, and metal. In accordance with some embodiments of the invention, the top layer and/or the base layer can range in thickness from 0.5 mm to 10 mm or more. In accordance with some embodiments of the invention, the separation chamber defining layer 214 and/or the exhaust chamber defining layer 218 can range in thickness from 0.01 mm to 10 mm or more. In accordance with some embodiments of the invention, the separation chamber defining layer can range in thickness from 0.025 mm to 0.075 mm to decrease dead volume and increase the likelihood of a bubble contacting the membrane.

As shown in FIG. 2, the bubble trap 120 can include a body 210 that includes a first body portion 212 and a second body portion 216. The first body portion 212 and the second body portion 216 can be fabricated from a range of biocompatible materials that can support cell culturing and resist absorption and/or adsorption of drugs and chemicals. These biocompatible materials can include acrylic, polystyrene, polypropylene, polycarbonate, styrene-ethylene/butylene-styrene (SEBS), polyurethane, silicones including, for example, Polydimethylsiloxane (PDMS), glass, epoxy-fiberglass, ceramic, metal, and combinations thereof. In accordance with some embodiments of the invention, the body portions 212, 216 portions of the bubble trap body 210 can be formed from combinations of materials, for example, combinations of layers of materials disclosed herein. In accordance with some embodiments, specific materials can be preferred for use with specific cell types and drug types. In accordance with some embodiments of the invention, one layer can be formed by combining two or more different materials, for example, where one portion of a layer can be fabricated from SEBS and the remainder of the layer can be formed from acrylic or one portion of a layer can be fabricated from an elastomeric formulation of SEBS and the remainder from a rigid formulation of SEBS In some embodiments where different materials are used for adjoining layers, the materials should be compatible with each other. The bubble trap 120, as an assembly of layers and body portions, can be held together by thread forming screws, nuts and bolts, clips, clamps, pins as well as or in addition to the use of heat staking, glue (e.g., biocompatible, low absorption adhesives), welding and various forms of bonding (e.g. thermal, solvent-activated, UV activated, ultrasonic).

In accordance with some embodiments of the invention, each of the layers can be fabricated by molding and/or machining (e.g., including mechanical cutting, laser cutting and etching) the various features into each layer. The layers can also be fabricated using rapid prototyping technologies, such as 3 dimensional printing and stereolithography. In accordance with some embodiments, 3 dimensional printing, stereolithography, and/or photolithography can be used to fabricate the mold forms that can be used to produce each of layers. Other well-known mold fabrication methods, such as machining, casting and stamping can also be used.

In accordance with some embodiments of the invention, the membrane 220 can be a hydrophobic porous membrane. The membrane 220 can include one or more layers that are fabricated from a hydrophobic material, such as, polytetrafluoroethylene (PTFE), expanded PTFE (e.g., GoreTex™), PTFE co-polymers, polyvinylidene fluoride (PVDF), PVDF co-polymers, polyphenylene sulfide, polybutenes, and silicones, such as Polydimethylsiloxane (PDMS). Other materials that can be used in the membrane 220 include hydrophobic formulations of polymers, such as, hydrophobic formulations of acrylics and polycarbonates. In accordance with some embodiments of the invention, the membrane can be fabricated from a non-hydrophobic material that is coated or treated to make the surface hydrophobic, for example, a PTFE coating or Slippery Liquid Infused Porous Surface (SLIPS) coating. SLIPS is described in PCT/US2012/021928, filed Jan. 19, 2011, which is hereby incorporated by reference in its entirety. In accordance with some embodiments of the invention, the membrane can be fabricated from a non-hydrophobic material that is bonded to a layer of material that provides a hydrophobic surface, for example, a PTFE layer or Slippery Liquid Infused Porous Surface (SLIPS) layer. In accordance with some embodiments of the invention, the membrane 220 can include a rigid material. In accordance with some embodiments of the invention, the membrane 220 can include a flexible and/or elastic material. In accordance with some embodiments of the invention, the membrane 220 can be treated to give the surface facing the separation chamber 222 of the membrane hydrophobic properties. The hydrophobic material repels the water based fluids flowing through the chamber 222, while the pores enable gas bubbles to pass through the membrane and become separated from the fluid. The size of the pores can be determined as function of the desired characteristics and performance of the membrane. Thus, while larger pores allow gas bubbles to pass through at lower fluid pressures (e.g., the differential between the fluid pressure and environmental pressure in the exhaust chamber 324 can affect the ability of bubble to pass through the membrane), the larger pores also provide increased diffusion and evaporation of the fluid through the membrane and are more susceptible to fluid leakage at lower pressures. Smaller pores require higher pressures to expel the gas bubbles, but help to reduce diffusion and evaporation losses of the fluid and resist fluid leakage at higher pressures. Thus, the selection of pore size and density can represent a balance that involves selecting the largest pore size and highest density that permits the gas bubbles to pass through the membrane with a minimum amount of acceptable fluid diffusion or evaporation and minimum acceptable fluid leakage at the system's operating pressure. The pores in the membrane can be formed by molding and/or machining (e.g., including mechanical cutting, laser cutting and etching) the pores into each layer that makes up the membrane 220.

In accordance with some embodiments of the invention, the membrane can have pores that range in size (the width dimension of the pores e.g., the diameter of circular pores) from 0.02 micrometers to 10 micrometers and in some embodiments as large as 50 micrometers. In accordance with some embodiments, the membrane can have pores in the range from 0.20 micrometers to 0.40 micrometers. The porosity of the membrane can range from 0.1% to 99%. As used herein, the term "porosity" is a measure of total void space (e.g., through-holes, openings, interstitial spaces, and/or hollow conduits) in a material, and is a fraction of volume of total voids over the total volume, as a percentage between 0 and 100% (or between 0 and 1). A membrane with substantially zero porosity is non-porous or non-permeable. The pores can be randomly or uniformly distributed (e.g., in an array or in a specific pattern, or in a gradient of pore sizes) over the membrane. In accordance with some embodiments of the invention, at least some or all of the pores can have a center-to-center pore spacing of about 1 μm to about 1000 μm, or about 10 μm to about 500 μm, or about 20 μm to about 100 μm. In one embodiment, at least some or all of the pores can have a center-to-center pore spacing of about 20 μm to about 50 μm. In accordance with some embodiments of the invention, the membrane can include a surface design or patterned (e.g., micro and/or nanoscopic patterns including grooves and/or ridges) for example, to guide the flow of fluid and/or bubbles, reduce turbulence and/or increase bubble removing efficiency or effectiveness.

The pores can extend through the membrane 220 from one surface to the opposite surface and can have any size and/or shape. For example, the pores of the membrane can have a pentagonal, circular, hexagonal, square, elliptical, oval, diamond, and/or triangular shape. While the pores preferably extend vertically (e.g., perpendicular to the membrane surface) between the top and bottom surfaces, they can extend laterally as well between the top and bottom surfaces membrane. It should also be noted that the pores can additionally/alternatively incorporate slits or other shaped apertures along at least a portion of the membrane 220 which allows gas bubbles to pass through the membrane 220 from the separation chamber 222 to the exhaust chamber 224.

In operation, the fluid and bubbles flow through the bubble trap 120 and a bubble comes in contact with the hydrophobic porous membrane 220 and wets the surface of the membrane. The fluid pressure that causes the fluid to flow through the bubble trap forces bubble through the membrane in to the exhaust chamber 224. In general, the pressure differential between the fluid pressure in the separation chamber 222 and the air pressure in the exhaust chamber 224 should be sufficient to enable the gas bubble to pass through the membrane. In accordance with some embodiments of the invention, the exhaust chamber can be connected to the ambient environment and the ambient environmental pressure can be sufficiently lower than the fluid pressure to enable the bubbles to pass through the membrane. In accordance with some embodiments of the invention, the pressure in the exhaust chamber can be controlled to ensure that it is low enough to enable the bubbles can pass through the membrane. The pressure differential needed to enable bubbles to pass through the membrane can vary and will be a function of the membrane characteristics as well as the surface tension of the fluid, the gas of the bubble and pressures in the separation chamber and the exhaust chamber.

In accordance with some embodiments of the invention, the bubble trap 120 can be fabricated by fabricating each layer of the device and then laminating using, for example, adhesive or other bonding method, the individual layers together, either in a single step or two layers at a time. In accordance with some embodiments of the invention, the bubble trap 120 can be fabricated by fabricating each layer of the device, arranging the layers in their intended configuration and then clamping or fastening the layers in place to form the device.

While in the illustrative examples, the bubble trap 120 is shown to include an inlet channel and an outlet channel, in an alternative embodiment of the invention, the bubble trap can be provided with a single channel that serves as both an inlet and an outlet. In operation, the fluid with gas bubbles can be pumped in to the separation chamber through the single channel to cause the gas bubbles to be forced out through the hydrophobic porous membrane and then the fluid without the bubbles can be drawn back out through the single channel.

FIG. 3A shows a diagrammatic cross-section view and FIG. 3B shows a top view of a bubble trap 120 according to an alternative embodiment of the invention. In accordance with some embodiments of the invention, the bubble trap 120 can be constructed by forming a gasketing embossment 332, 3344 in one surface of the first body portion 312 that defines a channel or chamber 322 and by positioning the membrane 320 of the bubble trap against the gasketing embossments 332, 334 to form a chamber or microfluidic channel 322 that extends over a portion of the membrane 320. The gasketing embossments 332, 334 can be pressed against the membrane 320 and form a seal that prevents the fluid from leaking out of the chamber 322. As shown in FIG. 3B, the gasketing embossments 332 and 334 can extend around and define the shape of the chamber 322. The chamber 322 can include an inlet port 342 enabling fluid to flow into the chamber 322 and an outlet port 344 to enable fluid to flow out of the chamber 322. Optionally, the bubble trap 120 can include an inlet channel 352 which directs the flow of fluid into the chamber 322 and an outlet channel 354 which directs the flow of fluid out of the chamber 322.

In accordance with some embodiments of the invention, one or more threaded fasteners can be used to compress the membrane 320 between the first body portion 312 and the second body portion 316. For example, threaded fasteners can extend through holes in the second body portion 316 and engage threaded holes in the first body portion 212 or nuts on the bottom of the first body portion 212. In accordance with some embodiments of the invention, the first body portion 312 and the second body portion 316 can be compressed against the membrane 320 by a clamping mechanism, such as in a housing or holder, not shown.

Figure 3C:
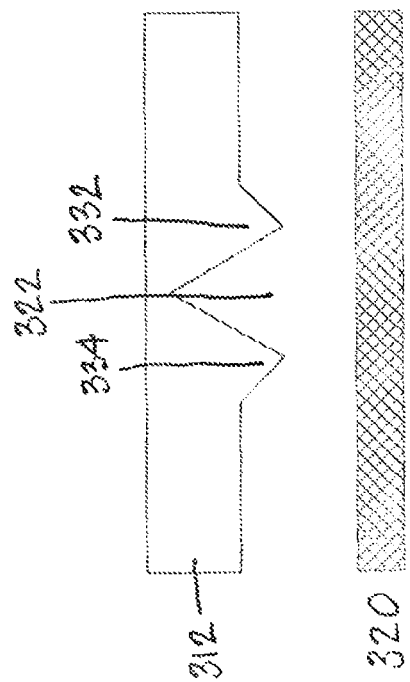
FIGS. 3C and 3D show diagrammatic views of a bubble trap formed by a gasketing embossment according to some alternative embodiments of the invention.
Figure 3D:
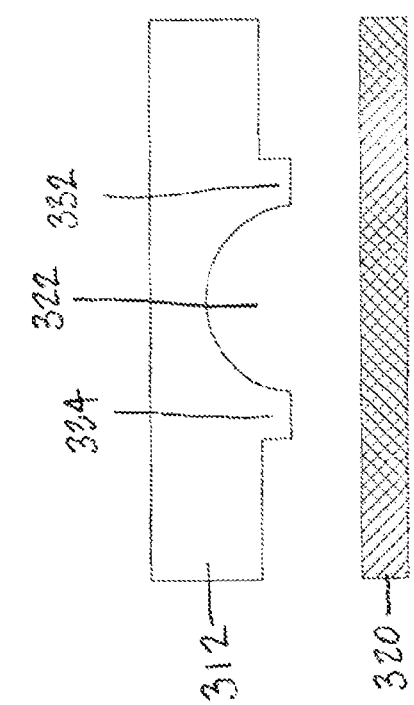

In accordance with some embodiments of the invention, a fluidic channel or chamber 322 can be formed by a gasketing embossment 332, 334 formed in one of the surfaces of one of the body portions 312, 316 of the bubble trap 120. In some embodiments one or more such channel or chamber 322 can be used to route fluid to one or more membranes 320. FIGS. 3C and 3D show diagrammatic detail views of gasketing embossments according to some embodiments of the invention. In accordance with some embodiments of the invention, the gasketing embossments can include one or more gasket features 332, 334 that project from the surface and form a channel feature 322, which can extend below the surface of the body portion 312. When the body 310 of the bubble trap 120 is assembled, the membrane 320 can be pressed against the gasket features 322, 334 sealing the channel feature 322 and forming the fluidic channel or chamber. In accordance with some embodiments of the invention, one or more gasketing embossments 332, 334 can be incorporated into the membrane 320. In accordance with some embodiments of the invention, as shown in FIG. 3C, the gasket features 322, 334 can provide a surface that contacts the membrane 320 and the channel feature 322 can have curved walls. In accordance with some embodiments of the invention, as shown in FIG. 3D, the gasket features 332, 334 can provide sharp or rounded features that contact the membrane 320 and the channel feature 322 can have flat walls. While the example shown in FIG. 3D shows the chamber 322 having a triangular shape, the chamber 322 can have rectangular shape or any desired shape.

In accordance with some embodiments of the invention, the gasketing embossments can be formed by conventional molding and/or machining techniques. In addition, the gasketing embossments can be formed using hot embossing and microthermoforming fabrication techniques.

Figure 3E:
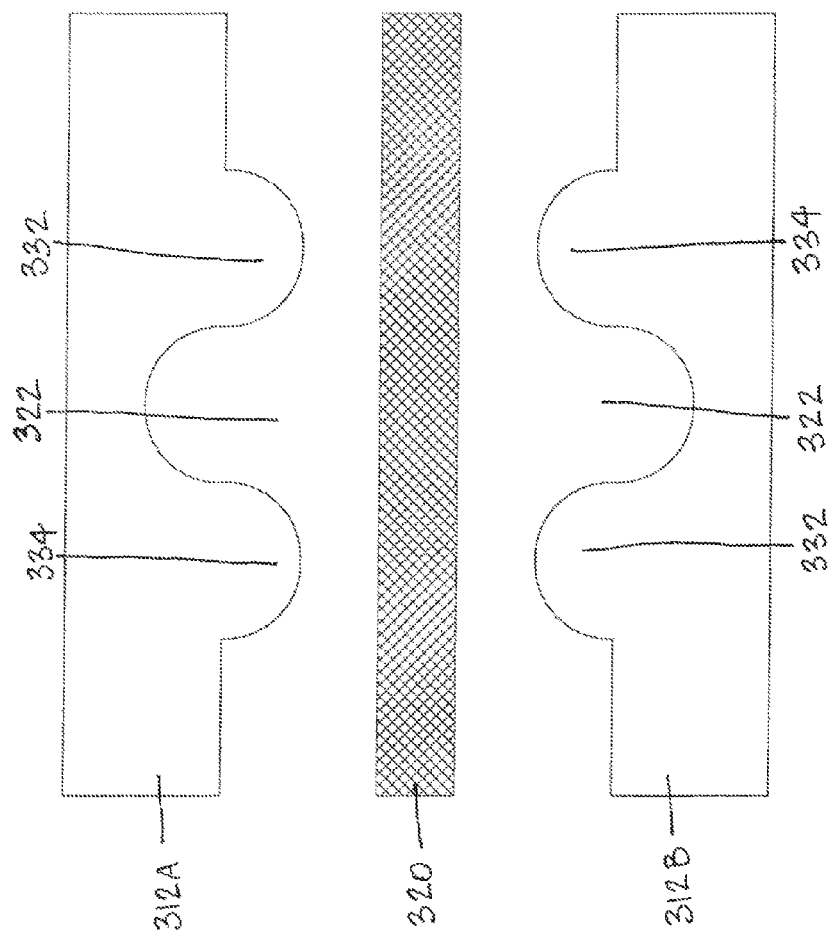
FIG. 3E shows a diagrammatic view of a bubble trap device formed by two adjoining gasketing embossments according to some embodiments of the invention.

FIG. 3E shows a diagrammatic sectioned view of an alternative embodiment of the functional area according to the invention. In accordance with some embodiments of the invention, the membrane 320 can be engaged on each side by a separate gasketing embossment 332A, 332B, 334A, 334B that forms a separate fluidic channel or chamber 322A, 322B one each side of the membrane. In accordance with some embodiments of the invention, the membrane 320 can be a selectively permeable membrane to enable the transfer of select gas ions or molecules between fluidic channels or chamber 322A, 322B.

FIG. 4A shows a diagrammatic view of a standalone bubble trap 120 according to the invention. FIG. 4B shows a diagrammatic exploded view of the bubble trap 120 shown in FIG. 4A. The bubble trap 120 can include a bubble trap body 410 that includes a first body portion 412, a second body portion 416 and a membrane 420. The bubble trap 120 can include one or more inlet channels or tubes 452 and one or more outlet channels or tubes 454. The inlet channels 452 can be connected to the inlet ports 442 to enable fluid to flow into the chamber 422 and outlet channels 454 can be connected outlet ports 444 to enable fluid to flow out of chamber 422. Gas bubbles that enter chamber 422 can pass through membrane 420 into exhaust chamber 424 and exit the bubble trap 120 through exhaust ports 446. The first body portion 412 and the second body portion 416 can be pressed against the membrane 420 by threaded fasteners 406 and 408. This configuration enables the membrane 420 to be replaced in the event that it fails or becomes clogged and to enable the chamber 422 and exhaust chamber 424 to be cleaned. In operation, tubing can be used to connect inlet channels or tubes 452 to a fluid source and outlet channels or tube 454 to a microfluidic device as shown in FIG. 1.

FIG. 5 shows a diagrammatic top view of a bubble trap 120 according to some embodiments of the invention. The bubble trap 120 can include a bubble trap body 510 that includes a closed exhaust chamber 524, similar to that shown in FIG. 2B. In accordance with some embodiments of the invention, the bubble trap body 510 can include one or more exhaust channels 562A, 562B that enable the air pressure in the exhaust chamber 524 to equalize to the ambient pressure and enable gas bubbles to pass through the membrane. At the same time, the exhaust channels can create an elongated path between the membrane and the free-stream air that can be used to limit evaporation losses through the membrane. This feature can be useful in systems that use small volumes of fluids as even small evaporative losses can change constituent concentrations and have a significant impact on the system performance.

Evaporation through a porous membrane in the bubble trap can be reduced by increasing the diffusion length or the distance that the water vapor travels from the membrane to the free-stream air. When all other variables are held constant, the magnitude of evaporation loss will decrease linearly with an increase in the diffusion length. The following calculation gives values for one embodiment of a bubble trap according to the invention.

$$J = -D\frac{\Delta C}{L} \quad (1)$$

Where j is the diffusion flux, D is the diffusion coefficient, delta C is the difference in water vapor concentration at the membrane and the end of the exhaust channel 562A, 562B, and L is the length of the exhaust channel 562A, 562B.

The concentration of water vapor at the porous membrane surface (e.g. 100% humidity, 2.4e-3 mol/m^3) and at the end of the air relief channel (e.g. 80% humidity incubator air, 1.9e-3 mol/m^3) at 37° C. can be determined from a psychometric chart. In one example of a bubble trap according to the invention, the exhaust channel 256A is 3 mm long. The diffusion coefficient of water vapor in air is 26.8e-6 m^2/s (Gates D. M., 1980, Biophysical Ecology, Springer, N.Y., pg 611). Using Eq. 1, the flux j is 4.5e-6 mol/(m$^2$*s).

The residence time of the fluid in the trap can be calculated using the following equation.

$$t_r = \frac{lwH}{Q} \quad (2)$$

Where $t_r$ is residence time, l is the length of the fluid channel, w is the width of the fluid channel, H is the height of the fluid channel, and Q is the flow rate. In one embodiment of the bubble trap the fluid channel is 21.5 mm long, 1 mm wide, and 0.15 mm deep. At a typical flow rate of 30 uL/hr this gives a fluid residence time in the bubble trap of 260 seconds. The surface area, S, for evaporation can be calculated using the area of the porous membrane in contact with fluid and its porosity, ε.

$$S = lw\varepsilon \quad (3)$$

A typical PTFE porous membrane filter has a porosity of 72%. Using Eq. 3, the surface area is approximately 15.5e-6 m². Multiplying the results of Eq. 1, Eq. 2, and Eq. 3 gives the molar loss of water for the residence time of the liquid in the bubble trap, about 1.81e-8 mol. Dividing the molar loss of water by the total molar volume of liquid in the trap (11.9e-5 mol) provides a measure evaporation loss, in this example, it is less than 0.02% of the total volume, which is an acceptable amount of evaporation for cell culture media for this example.

While the figures show the membrane 220, 320, 420, 520 in a substantially planar configuration, the membrane can also be configured and used in a non-planar configuration. The membrane 220, 320, 420, 520 can be configured to conform to any channel or chamber wall shape. The membrane 220, 320, 420, 520 can be configured with ripples or pleats that provide additional surface area through which bubbles can pass.

Figure 6:
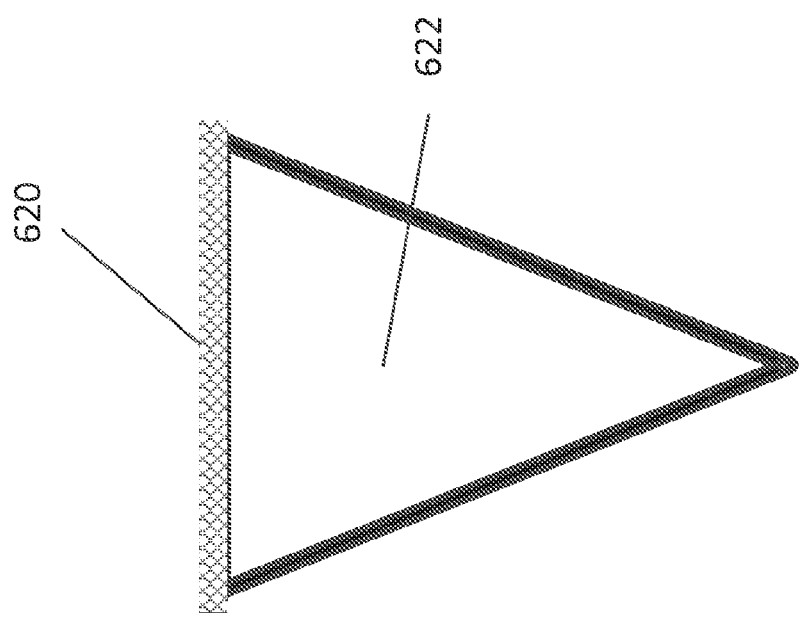
FIG. 6 shows a diagrammatic view of a bubble trap device having a triangular separation chamber according to some embodiments of the invention.
Figure 7:
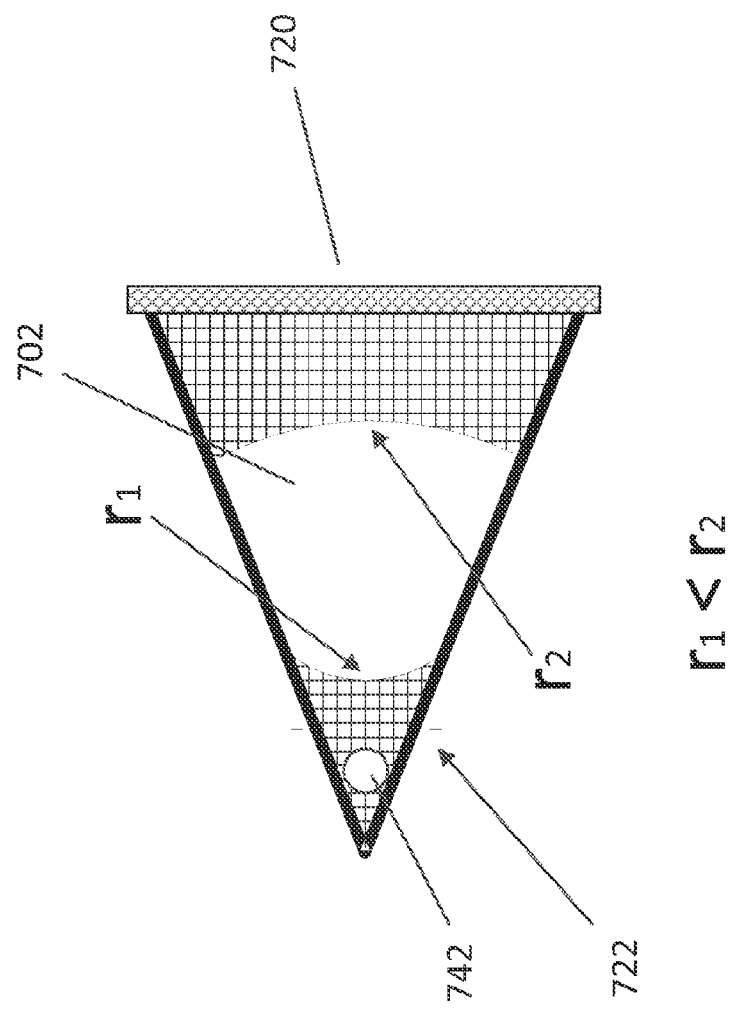
FIG. 7 shows a diagrammatic view of a bubble trap device having a triangular separation chamber according to some embodiments of the invention.

While the figures show the channel or chamber 222, 322, 422 having both an inlet channel and an outlet channel, the bubble trap of the present invention can be configured with a single channel through which fluid flows into and out of the channel or chamber 222, 322, 422. In this embodiment, fluid can flow into the channel or chamber 222, 322, 422 whereby the fluid pressure forces the air bubbles out through the membrane 220, 320, 420, and then the fluid can be extracted through the same channel;

While the figures show the channel or chamber 222, 322, 422, as having a substantially rectangular cross-sectional shape, the cross-sectional shape of the channel or chamber 222, 322, 422 can be circular, oval, elliptical, triangular, trapezoidal or a combination thereof. In accordance with some embodiments the channel or chamber 222, 322, 422 can be triangular as shown in FIGS. 6 and 7. In this configuration, the gas bubbles can come in contact with more than one wall of the channel or chamber 222, 322, 422, each having a membrane and increasing the likelihood that the gas will contact the membrane so that it can be removed. In accordance with other embodiments of the invention, the channel or chamber 222, 322, 422 can taper in one dimension while expanding in another dimension to increase the likelihood that the gas will contact the membrane so that it can be removed without changing the cross-sectional area of the channel or chamber 222, 322, 422 so the flow rate does not change.

FIG. 6 shows bubble trap 120 that includes a separation chamber 622 having a triangular shape. In accordance with some embodiments of the invention, the triangular separation chamber 622 can include the membrane 620 at the top of the chamber allowing the bubbles to through the top of the bubble trap 120. However, it not necessary for the membrane 620 to be positioned at the top of the separation chamber 622.

In accordance with some embodiments the invention, the membrane can be located in positions other than the top of the separation chamber. The Bond number provides a measure of the surface tension forces of the fluid as compared to the gravitational forces. The Bond number can be determined by the following equation.

$$Bo = \frac{\rho a L^2}{\gamma} \quad (4)$$

Where, Bo is the bond number, ρ is the density or density difference between fluids, a is the acceleration associated with the body force, typically gravity, L is the 'characteristic length scale', e.g. radius of a drop or the radius of a capillary tube, and γ is the surface tension of the interface. A high Bond number (e.g., Bo>1) indicates that gravity dominates the system and bubbles will rise due to buoyancy. A low Bond number (e.g., Bo<1) indicates that the surface tension dominates the system and the bubble may not rise to the top.

FIG. 7 shows bubble trap 120 that includes a separation chamber 722 having a triangular shape. In accordance with some embodiments of the invention, the triangular separation chamber 722 can include the membrane 720 which is not at the top of the chamber 722. In this embodiment, the chamber inlet 742 and the chamber outlet 744 can be positioned adjacent the corner opposite the membrane 720 and provide a flow path along the corner of the chamber 720. This embodiment utilizes the property that the pressure due to the curvature of the gas-liquid interface scales with the inverse of the radius. As shown in FIG. 7, the $r_2$ is greater than $r_1$ so that the pressure differential due to the different radii pushes the bubble away from flow path in the corner toward the membrane 720.

Figure 8:
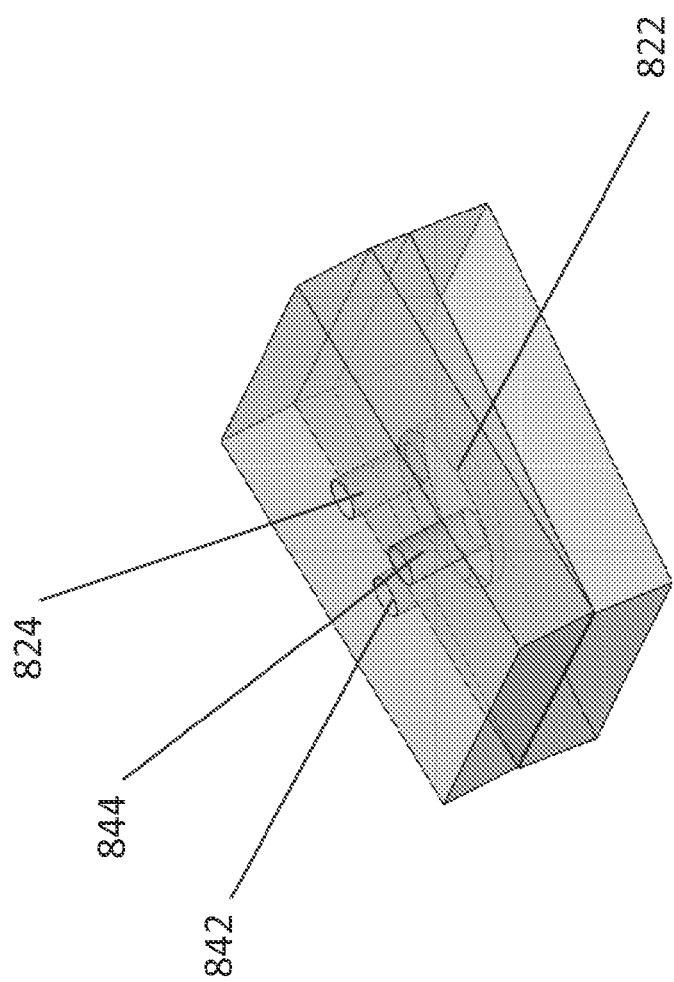
FIG. 8 shows a diagrammatic view of a bubble trap device having a triangular separation chamber according to some embodiments of the invention.

FIG. 8 shows bubble trap 120 that includes a separation chamber 822 having a triangular shape. In accordance with some embodiments of the invention, the triangular separation chamber 822 that includes an inlet port 842, an outlet port 844 and an exhaust chamber 824 on the same surface. The membrane (not shown) can be on the inside of the separation chamber at the bottom of the exhaust chamber 824. In this embodiment, fluid enters the separation chamber 822 through inlet port 842 and exits the separation chamber 822 through outlet port 844 and gas from the bubbles is vented through exhaust chamber 824.

In accordance with some embodiments of the invention, the bubble trap can be formed from a tubular structure in which all or substantially all the sides of the bubble trap include a hydrophobic porous membrane or a portion of the hydrophobic porous membrane. In accordance with some embodiments of the invention, the hydrophobic porous membrane can be formed in a tube. The tube can have a round or oval cross-section as well as a triangular, rectangular, or other polygonal shape.

The subject matter of the present invention can be defined by any of the following paragraphs:

A. A microfluidic system comprising:
a microfluidic device comprising
a body having a central microchannel and membrane mounting regions adjacent to the central microchannel, the central microchannel having an inlet for introducing fluid to the central channel;
a porous membrane extending generally along a plane across the central microchannel and separating the central microchannel into a first microchannel and a second microchannel, the porous membrane being coupled to the body at the membrane-mounting regions, the porous membrane including a first side facing toward the first micro channel and a second side facing toward the second microchannel, the first side having cells of a first type adhered thereto;
a bubble trap comprising a separation chamber and an exhaust chamber separated by a hydrophobic porous membrane, the separation chamber being connected to a fluid channel and the fluid channel being connected to the inlet of the microfluidic device, wherein fluid and gas bubbles can enter the separation chamber and fluid from the separation chamber flows through the fluid channel to the inlet of the microfluidic device and gas bubbles pass through the hydrophobic porous membrane into the exhaust chamber.

B. The microfluidic system according to paragraph B wherein the bubble trap further comprises a fluid inlet; and wherein fluid and gas bubbles can enter the separation chamber through the fluid inlet; and fluid from the separation chamber flows through the fluid channel to the inlet of the microfluidic device and gas bubbles pass through the hydrophobic porous membrane into the exhaust chamber.

C. The microfluidic system according to paragraph A or B wherein the exhaust chamber is open to an ambient atmosphere of the microfluidic system.

D. The microfluidic system according to any of paragraphs A-C wherein the exhaust chamber is connected to the ambient atmosphere by an exhaust channel that limits evaporation losses through the hydrophobic porous membrane.

E. The microfluidic system according to any of paragraphs A-D wherein the exhaust chamber is coupled to a chamber for capturing the gas from the gas bubbles that pass through the hydrophobic porous membrane.

F. The microfluidic system according to any of paragraphs A-E wherein the bubble trap comprises a first body portion bonded to a first side of the hydrophobic porous membrane and a second body portion bonded to a second side of the hydrophobic porous membrane.

G. The microfluidic system according to any of paragraphs A-F wherein the hydrophobic porous membrane includes polytetrafluoroethylene (PTFE).

H. The microfluidic system according to any of paragraphs A-G wherein the hydrophobic porous membrane includes pores that range in size from 0.02 micrometers to 10 micrometers.

I. The microfluidic system according to any of paragraphs A-H wherein the hydrophobic porous membrane includes pores that range in size from 0.20 micrometers to 0.40 micrometers.

J. The microfluidic system according to any of paragraphs A-I wherein the hydrophobic porous membrane includes pores having a center to center pore spacing of 1.0 micrometers to 1000 micrometers.

K. The microfluidic system according to any of paragraphs A-J wherein the hydrophobic porous membrane includes pores having a center to center pore spacing of 20 micrometers to 100 micrometers.

L. The microfluidic system according to any of paragraphs A-K wherein at least a portion of the separation chamber has a triangular cross-section.

M. The microfluidic system according to any of paragraphs A-L wherein the separation chamber includes an upper most surface and the hydrophobic porous membrane is positioned on a surface of the separation chamber below the upper most surface of the separation chamber.

N. The microfluidic system according to any of paragraphs A-M wherein the second side of the porous membrane includes cells of second type adhered thereto.

O. The microfluidic system according to any of paragraphs A-N wherein at least one side of the porous membrane includes a cell adhesion promoting material and the cell adhesion material is selected from the group including ECM proteins, fibronectin, laminin, vitronectin or tenascin.

P. The microfluidic system according to any of paragraphs A-O wherein the second side includes a biologic fluid and the biologic fluid is selected from the group including water, saline, blood, cell culture media.

Q. A bubble trap comprising:

a separation chamber formed on a first side of the hydrophobic porous membrane by bonding a first body portion the first side of a hydrophobic porous membrane; and an exhaust chamber formed on a second side of the hydrophobic porous membrane by bonding a second body portion the second side of the hydrophobic porous membrane.

R. The bubble trap according to paragraph Q wherein the first body portion includes the separation chamber formed by machining a channel in one side of first body portion.

S. The bubble trap according to paragraph Q or R wherein the first body portion includes the separation chamber formed by bonding a separation chamber defining layer to a base layer.

T. The bubble trap according to any of paragraphs Q-S wherein the separation chamber defining layer includes an adhesive material.

U. The bubble trap according to any of paragraphs Q-T wherein the separation chamber defining layer includes an elastic material.

V. The bubble trap according to any of paragraphs Q-U wherein the second body portion includes the exhaust chamber formed by machining a channel in one side of second body portion.

W. The bubble trap according to any of paragraphs Q-V wherein the second body portion includes the exhaust chamber formed by bonding an exhaust chamber defining layer to a top layer.

X. The bubble trap according to any of paragraphs Q-W wherein the exhaust chamber defining layer includes an adhesive material.

Y. The bubble trap according to any of paragraphs Q-X wherein the exhaust chamber defining layer includes an elastic material.

Z. A bubble trap comprising:

a separation chamber formed on a first side of the hydrophobic porous membrane by compressing a first body portion against the first side of a hydrophobic porous membrane; and an exhaust chamber formed on a second side of the hydrophobic porous membrane by compressing a second body portion against the second side of the hydrophobic porous membrane.

AA. The bubble trap according to paragraph Z wherein the first body portion includes the separation chamber formed by machining a channel in one side of first body portion.

BB. The bubble trap according to paragraph Z or AA wherein the first body portion includes the separation chamber defined by a gasketing embossment formed in the first body portion, the gasketing embossment being compressed against the hydrophobic porous membrane.

CC. The bubble trap according to any of paragraphs Z-BB wherein the second body portion includes the exhaust chamber formed by machining a channel in one side of second body portion.

DD. The bubble trap according to any of paragraphs Z-CC wherein the second body portion includes the exhaust chamber defined by a gasketing embossment formed in the second body portion, the gasketing embossment being compressed against the hydrophobic porous membrane.

EE. The bubble trap according to any of paragraphs Z-DD wherein the first body portion is compressed against the hydrophobic porous membrane by one or more threaded fasteners.

FF. The bubble trap according to any of paragraphs Z-EE wherein the first body portion is compressed against the hydrophobic porous membrane by one or more clamps.

Other embodiments are within the scope and spirit of the invention. For example, due to the nature of the microfluidic system, components and devices described above can be implemented using discrete components and devices as well as in a single integrated system and a wide range of combinations of integrated components and devices and discrete components and devices. Features implementing functions may also be physically located at various positions, including being distributed such that portions of functions are implemented at different physical locations.

Further, while the description above refers to the invention, the description may include more than one invention.

What is claimed is:

1. A microfluidic system comprising:
   a microfluidic device comprising
      a microchannel
      including cells of a first type adhered thereto; and
   a bubble trap comprising
      a first body comprising a separation chamber that is defined by a first set of gasketing embossments that project from the surface of the first body, and that are compressed against the first side of a porous membrane such that the separation chamber is below the first side of the porous membrane, and connected to a fluid channel and the fluid channel being connected to the microfluidic device, and
      a second body comprising an exhaust chamber that is defined by a second set of gasketing embossments that project from the surface of the second body, and that are compressed against the second side of the porous membrane such that the exhaust chamber is above the second side of the porous membrane and open to an ambient atmosphere of the microfluidic system,
   wherein the microfluidic device is configured such that fluid and gas bubbles can enter the separation chamber and fluid from the separation chamber flows through the fluid channel to the microfluidic device and gas bubbles pass through the porous membrane into the exhaust chamber.

2. The microfluidic system according to claim 1 wherein the bubble trap further comprises a fluid inlet; and
   wherein fluid and gas bubbles can enter the separation chamber through the fluid inlet.

3. The microfluidic system according to claim 1 wherein the exhaust chamber is connected to the ambient atmosphere by an exhaust channel that limits evaporation losses through the porous membrane.

4. The microfluidic system according to claim 1 wherein the bubble trap comprises a first body portion bonded to a first side of the porous membrane and a second body portion bonded to a second side of the porous membrane.

5. The microfluidic system according to claim 1 wherein the porous membrane is a hydrophobic membrane.

6. The microfluidic system according to claim 1 wherein the separation chamber includes an upper most surface and the porous membrane is positioned on a surface of the separation chamber above the upper most surface of the separation chamber.

7. A bubble trap comprising:
   a first body comprising a separation chamber that is defined by a first set of gasketing embossments that project from the surface of the first body, and that are compressed against the first side of a porous membrane such that the separation chamber is formed below a porous membrane by bonding the first body to the first side of the porous membrane; and
   a second body comprising an exhaust chamber that is defined by a second set of gasketing embossments that project from the surface of the second body, and that are compressed against the second side of the porous membrane such that the exhaust chamber is formed above the porous membrane by bonding the second body to the second side of the porous membrane.

8. The bubble trap according to claim 7 wherein the first body portion includes the separation chamber formed by machining a channel in one side of first body portion.

9. The bubble trap according to claim 7 wherein the first body portion includes the separation chamber formed by bonding a separation chamber defining layer to a base layer.

10. The bubble trap according to claim 9 wherein the separation chamber defining layer includes an adhesive material.

11. The bubble trap according to claim 9 wherein the separation chamber defining layer includes an elastic material.

12. The bubble trap according to claim 7 wherein the second body portion includes the exhaust chamber formed by machining a channel in one side of second body portion.

13. The bubble trap according to claim 7 wherein the second body portion includes the exhaust chamber formed by bonding an exhaust chamber defining layer to a top layer.

14. A bubble trap comprising:
   a first body comprising a separation chamber that is defined by a first set of gasketing embossments that project from the surface of the first body, and that are compressed against the first side of a porous membrane such that the separation chamber is below the first side of the porous membrane; and
   a second body comprising an exhaust chamber that is defined by a second set of gasketing embossments that project from the surface of the second body, and that are compressed against the second side of the porous membrane such that the exhaust camber is above the second side of the porous membrane.

15. A microfluidic system comprising:
   a microfluidic device comprising
      a microchannel
      comprising cells of a first type adhered thereto; and
   a bubble trap comprising
      a first body comprising a separation chamber having walls, more than one wall having a porous membrane such that gas bubbles can come in contact with more than one of the porous membranes, the separation chamber being connected to a fluid channel and the fluid channel being connected to the microfluidic device, and
      a second body comprising an exhaust chamber above the second side of the porous membrane and open to an ambient atmosphere of the microfluidic system,
   wherein one or both of the separation chamber and the exhaust chamber are defined by a set of gasketing embossments that project from the surface of the first body and the second body, respectively, wherein the gasketing embossments are compressed against the first side and the second side, respectively, of the porous membrane, and wherein the microfluidic device is configured such that fluid and gas bubbles can enter the separation chamber and fluid from the separation chamber flows through the fluid channel to the microfluidic device and gas bubbles pass through at least one of the porous membranes.

16. The microfluidic system of claim 15, wherein the separation chamber has a triangular shape.

17. A microfluidic system comprising:
a microfluidic device comprising cells of a first type adhered thereto; and
a bubble trap comprising
a first body comprising a separation chamber connected to a fluid channel and the fluid channel being connected to the microfluidic device, and
a second body comprising an exhaust chamber connected to an elongated exhaust channel that is configured to increase the diffusion distance from the porous membrane to the ambient environment,
wherein one or both of the separation chamber and the exhaust chamber are defined by a set of gasketing embossments that project from the surface of the first body and the second body, respectively, wherein the gasketing embossments are compressed against the first side and the second side, respectively, of the porous membrane, and
wherein the microfluidic device is configured such that fluid and gas bubbles can enter the separation chamber and fluid from the separation chamber flows through the fluid channel to the microfluidic device and gas bubbles pass through the porous membranes into the exhaust chamber and into the exhaust channel.

18. The microfluidic system of claim 17, wherein the exhaust channel is connected to the ambient environment by the elongated exhaust channel.

19. A microfluidic system comprising:
a microfluidic device comprising cells of a first type adhered thereto; and
a bubble trap comprising
a first body comprising a separation chamber tapered in one dimension while expanding in another dimension and being connected to a fluid channel, the fluid channel being connected to the microfluidic device, and
a second body comprising an exhaust chamber above the second side of the porous membrane and open to an ambient atmosphere of the microfluidic system,
wherein one or both of the separation chamber and the exhaust chamber are defined by a set of gasketing embossments that project from the surface of the first body and the second body, respectively, wherein the gasketing embossments are compressed against the first side and the second side, respectively, of the porous membrane, and
wherein the microfluidic device is configured such that fluid and gas bubbles enter the separation chamber and fluid from the separation chamber flows along a flow path through the fluid channel to the microfluidic device, the gas bubbles having first and second radii due to the shape of the separation chamber such that the pressure differential due to the different radii pushes the gas bubbles away from the flow path in a corner of the bubble trap toward the porous membrane resulting in the gas bubbles passing through the porous membrane.

20. The microfluidic system of claim 19, wherein the separation chamber has a triangular shape.

21. The bubble trap of claim 14, wherein the separation chamber has a triangular shape.

22. A bubble trap comprising
a first body comprising a separation chamber that has a triangular cross section and is defined by a first set of gasketing embossments that are compressed against the first side of a porous membrane, wherein the separation chamber is configured to separate bubbles that do not rise to the top of the separation chamber, and wherein the first side of the membrane is not at the top of the separation chamber, and
a second body comprising an exhaust chamber that is defined by a second set of gasketing embossments that are compressed against the second side of the porous membrane.

23. The bubble trap of claim 22, wherein the separation chamber comprises an inlet and an outlet that are positioned adjacent the corner opposite the membrane and that are configured to provide a flow path along the corner opposite the membrane, and to generate a pressure differential on bubbles in the flow path such that the pressure differential pushes the bubbles away from the flow path toward the membrane.

24. A method for making the bubble trap of claim 14, comprising
a) providing
i) the first body comprising the first set of gasketing embossments that project from the surface of the first body,
ii) the second body comprising the second set of gasketing embossments that project from the surface of the second body, and
iii) the porous membrane having a first side and a second side,
b) positioning the first set of gasketing embossments against the first side of the porous membrane to form the separation chamber that is defined by the first set of gasketing embossments, and that extends below the first side of the porous membrane, and
c) positioning the second set of gasketing embossments against the second side of the porous membrane to form the exhaust chamber that is defined by the second set of gasketing embossments, and that extends above the second side of the porous membrane, thereby making the bubble trap of claim 14.

25. A microfluidic device comprising:
a first body having a first surface and comprising a first chamber; and
a second body having a second surface and comprising a second chamber,
wherein the first surface of the first body is in contact with the second surface of the second body such that the first chamber and the second chamber form a fluidic channel,
wherein one or both of the first chamber and the second chamber are defined by a set of gasketing embossments that project, respectively, from the first surface of the first body and from the second surface of the second body, and
wherein the gasketing embossments of the first surface are compressed against the second surface, and the gasketing embossments of the second surface are compressed against the first surface.

* * * * *